United States Patent [19]

Brima et al.

[11] 4,400,324

[45] Aug. 23, 1983

[54] PROCESS FOR PREPARING ANTHRAQUINONE

[75] Inventors: Thomas S. Brima, Cincinnati, Ohio; Auburn B. Cottingham, Lake Elmo, Minn.

[73] Assignee: National Distillers and Chemical Corporation, New York, N.Y.

[21] Appl. No.: 288,825

[22] Filed: Jul. 31, 1981

[51] Int. Cl.$^3$ .............................................. C07C 97/24
[52] U.S. Cl. .................................... 260/369; 252/465
[58] Field of Search ........................ 260/369; 252/465

[56] References Cited

U.S. PATENT DOCUMENTS

| | | | |
|---|---|---|---|
| 1,890,040 | 12/1932 | Cüttringhous et al. | 260/369 |
| 2,072,867 | 3/1937 | Carothers | 260/369 |
| 2,264,429 | 12/1941 | Bergmann | 260/369 |
| 2,453,327 | 11/1948 | Layng et al. | 252/465 |
| 2,536,833 | 1/1951 | Bailey | 260/396 R |
| 2,652,408 | 9/1953 | Lecher et al. | 260/369 |
| 2,769,847 | 11/1956 | Robinson | 252/472 |
| 2,938,913 | 5/1960 | Weyker et al. | 260/369 |
| 3,150,930 | 9/1964 | Hiratsuka et al. | 260/369 |
| 3,655,741 | 4/1972 | Sturm et al. | 260/369 |
| 3,699,134 | 10/1972 | Armbrust et al. | 260/369 |
| 3,963,601 | 6/1976 | Hilfman | 252/442 |
| 4,045,456 | 8/1977 | Merger et al. | 260/369 |

*Primary Examiner*—Delbert E. Gantz
*Assistant Examiner*—Raymond Covington
*Attorney, Agent, or Firm*—Kenneth D. Tremain

[57] ABSTRACT

A process for preparing anthraquinone is disclosed which comprises reacting 1,3-butadiene with oxygen in the presence of a catalytically effective amount of a catalyst comprising a mixed metal oxide containing aluminum, molybdenum and titanium values.

9 Claims, No Drawings

PROCESS FOR PREPARING ANTHRAQUINONE

BACKGROUND OF THE INVENTION

1. Field of the Invention

This invention relates to processes for preparing anthraquinone and, in particular, to a process for preparing anthraquinone by the catalyzed vapor phase reaction of 1,3-butadiene and oxygen.

2. Description of the Prior Art

Anthraquinone, which in the pure state is a pale yellow, crystalline solid melting at 286° C. and boiling at 379°–381° C. at atmospheric pressure, and is represented by the structural formula,

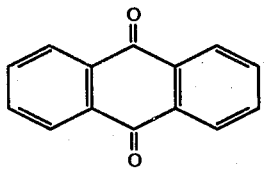

is a valuable intermediate for the manufacture of a variety of dyes. Commercially, anthraquinone is produced by several methods, e.g., the oxidation of anthracene employing sodium dichromate and sulfuric acid; the direct catalyzed oxidation of anthracene with air or other oxygen-containing material; and, the reaction of phthalic anhydride with benzene in the presence of aluminum chloride followed by acid cyclization of the intermediate product. Still another synthesis of anthraquinone is based upon the Diels-Alder reaction of 1,3-butadiene with a mixture of naphthalene, phthalic anhydride and 1,4-naphthoquinone obtained from the vapor phase oxidation of naphthalene (viz. U.S. Pat. Nos. 1,890,040; 2,536,833; 2,652,408 and 2,938,913).

SUMMARY OF THE INVENTION

It has now been discovered that anthraquinone can be readily and conveniently prepared by the vapor phase reaction of 1,3-butadiene with oxygen in the presence of a catalytically effective amount of a substantially water-insoluble mixed metal oxide catalyst containing the elements aluminum, molybdenum and titanium.

The term "mixed metal oxide" as used herein is to be understood in its art-recognized sense, i.e., as a combination of individual metal oxides which are more intimately associated with each other than the individual metal oxides of a mere mechanical mixture (viz. U.S. Pat. No. 2,769,847).

DESCRIPTION OF THE PREFERRED EMBODIMENTS

The starting 1,3-butadiene herein can be substantially pure but, more usually, will be of industrial or commercial quality, i.e., in admixture with minor amounts of one or more impurities.

The source of oxygen herein is not critical and includes pure oxygen, enriched air and atmospheric air, the latter being preferred for reasons of economy and convenience. It is advantageous to use a large stoichiometric excess of oxygen, e.g., from about 1.5 to 5 times the theoretical amount needed, care, of course, being observed not to provide an explosive mixture.

The reaction herein most readily occurs in the vapor phase and at elevated temperatures. Pressures of up to 5,000 psig and preferably, pressures ranging from atmospheric to 1,000 psig, can be used with good results. Temperatures can be widely varied and in general will be in the range of from about 100° C. to about 500° C., and preferably, from about 200° C. to about 400° C.

The reaction can be carried out on a batch or continuous basis, the latter being more readily suitable to low-cost operation. The process herein contemplates the use of known and conventional oxidation-resistant apparatus which is commercially available from numerous sources.

The mixed metal oxide catalyst herein must contain aluminum, molybdenum and titanium values and optionally can be supported upon an inert inorganic carrier such as silica, silica gel, titania, zirconia, alumina, and the like. The atomic ratio of aluminum:molybdenum:titanium is advantageously selected to be within the range of from about 0.1:1:0.1 to about 10:1:10 and preferably from about 1:1:1 to about 5:1:5.

The amount of mixed metal oxide catalyst employed can vary widely, with quantities being selected such as to provide a suitable range of superficial contact time, e.g., from a few seconds to a few minutes or more, under the prevailing reaction conditions. The relationship between superficial contact time, catalyst volume and reaction conditions is given by the equation:

$$\text{Superficial Contact Time} = \frac{\text{Volume Catalyst}}{\text{Total Vol. feed gases} \times \frac{T_1}{T_2} \times \frac{P_1}{P_2}}$$

Thus, for example, given a catalyst volume of 50 ml, a total feed gas volume of 200 ml/min (160 ml/min air and 40 ml/min 1,3-butadiene), $T_1$=reaction temp. (Å)=273+250=523 Å, $T_2$=ambient temp.=25+273=298 Å (temp. at which flow rate is measured) and pressure $P_1$=pressure $P_2$ (reaction pressure=atmospheric=pressure at which the flow rate is measured), the superficial contact time is 8.55 seconds.

In a preferred process for providing a suitably active mixed metal oxide catalyst, a titanium halide such as titanium tetrachloride is reacted with aluminum hydroxide and the resulting solid reaction product is thereafter reacted with ammonium heptamolybdate to provide a solid which, after being optionally deposited upon a carrier such as any of those aforementioned, is calcined, preferably in an inert of oxygen-containing atmosphere and preferably below about 500° C., to yield the desired catalyst.

In the examples which follow, Example 1 is illustrative of the preparation of the aluminum-molybdenum-titanium-containing mixed metal oxide catalyst herein and Example 2 illustrates the use of said catalyst in the oxidation of 1,3-butadiene to provide anthraquinone.

EXAMPLE 1

Preparation of Al/Ti/Mo Mixed Metal Oxide

To a reaction vessel provided with a condenser and a blanket of dry nitrogen was added 39 g aluminum hydroxide in 130 ml toluene and 55 ml titanium tetrachloride. Reaction commenced almost instantaneously. The contents of the flask were subjected to vigorous stirring and the evolution of gas was observed. Stirring was continued at room temperature for about 16 hours. The contents of the vessel were then heated to about 80° C. for an additional 20 hours. After cooling to room temperature, the contents were filtered, the recovered solid was washed copiously with toluene and the damp-dry powder was transferred to a dessicator in which it was dried under vacuum for three hours. Half (51 g) the resulting brown solid was combined with finely powdered ammonium heptamolybdate tetrahydrate (16.3 g) in 150 mls toluene. The mixture was stirred overnight and left at room temperature for nearly two days. Following reflux for two hours and removal of the toluene, a grayish powder was recovered. The powder was pelletized with 25 g alumina and calcined in air at 400° C. for 16 hours to provide the catalyst herein.

EXAMPLE 2

Oxidation of 1,3-Butadiene to provide Anthraquinone 1,3-Butadiene gas at the rate of 4.7 g butadiene/hour and atmospheric air at the rate of 160 ml/min was introduced into a reactor equipped with a trap and containing 50 ml of the mixed metal oxide catalyst prepared in Example 1. Reaction was carried out at 250° C.±20° C. for 2 hours. The amount of 1,3-butadiene recovered was 6.0 g for a conversion of this reactant of 36.2%. The crude product which collected in the ice-cooled trap was partially crystalline. About 10 ml of acetone was added to the trap and the solid product was collected by filtration; m.p. 266°–273° C. Its infra-red spectrum identified the solid as anthraquinone.

What is claimed is:

1. A process for preparing anthraquinone which comprises reacting 1,3-butadiene with an oxygen-containing material in the presence of a catalytically effective amount of a catalyst comprising a mixed metal oxide containing aluminum, molybdenum and titanium values.
2. The process of claim 1 wherein the oxygen-containing material is atmospheric air.
3. The process of claim 1 wherein the reaction is carried out in the vapor phase at atmospheric pressure.
4. The process of claim 3 wherein the reaction is carried out at from about 100° C. to about 500° C.
5. The process of claim 4 wherein the reaction is carried out at from about 200° C. to about 400° C.
6. The process of claim 1 wherein the catalyst consists essentially of a mixed metal oxide of aluminum, molybdenum and titanium.
7. The process of claim 1 wherein the atomic ratio of aluminum:molybdenum:titanium is from about 0.1:1:0.1 to about 10:1:10.
8. The process of claim 1 wherein the atomic ratio of aluminum-molybdenum:titanium is from about 1:1:1 to about 5:1:5.
9. The process of claim 1 wherein the mixed metal oxide is prepared by the process which comprises reacting titanium halide with aluminum hydroxide, reacting the resulting solid reaction product with ammonium heptamolybdate and thereafter calcining the recovered solid in an inert or oxygen-containing atmosphere.

* * * * *